United States Patent
Wyatt

(10) Patent No.: US 7,539,623 B1
(45) Date of Patent: May 26, 2009

(54) METHOD AND A SYSTEM FOR PROVIDING BED AVAILABILITY INFORMATION ON A COMPUTER NETWORK

(75) Inventor: Phil Wyatt, Highland Park, IL (US)

(73) Assignee: Medical Central Online, Lake Forest, IL (US)

( * ) Notice: Subject to any disclaimer, the term of this patent is extended or adjusted under 35 U.S.C. 154(b) by 938 days.

(21) Appl. No.: 09/544,508

(22) Filed: Apr. 6, 2000

(51) Int. Cl.
G06Q 10/00 (2006.01)
G06Q 50/00 (2006.01)

(52) U.S. Cl. .................. 705/5; 705/2; 705/28
(58) Field of Classification Search ............ 705/5, 705/6, 2, 3, 28; 379/143
See application file for complete search history.

(56) References Cited

U.S. PATENT DOCUMENTS

| | | | |
|---|---|---|---|
| 4,135,241 A * | 1/1979 | Stanis et al. ............. | 705/2 |
| 5,669,005 A | 9/1997 | Curbow et al. | |
| 5,717,945 A | 2/1998 | Tamura | |
| 5,784,625 A | 7/1998 | Walker | |
| 5,826,237 A | 10/1998 | Macrae et al. | |
| 5,835,712 A | 11/1998 | DuFresne | |
| 5,848,427 A | 12/1998 | Hyodo | |
| 5,878,262 A | 3/1999 | Shoumura et al. | |
| 5,884,321 A | 3/1999 | Meffert | |
| 5,911,145 A | 6/1999 | Arora et al. | |
| 5,933,828 A | 8/1999 | Eitel et al. | |
| 5,940,834 A | 8/1999 | Pinard et al. | |
| 5,950,207 A | 9/1999 | Mortimore et al. | |
| 5,953,724 A | 9/1999 | Lowry | |
| 5,956,704 A | 9/1999 | Gautam et al. | |
| 5,956,720 A | 9/1999 | Fernandez et al. | |
| 5,956,737 A | 9/1999 | King et al. | |
| 5,966,717 A | 10/1999 | Sass | |
| 5,974,430 A | 10/1999 | Mutschler, III et al. | |
| 5,974,431 A | 10/1999 | Iida | |
| 5,983,227 A | 11/1999 | Nazem et al. | |
| 5,991,534 A | 11/1999 | Hamilton et al. | |

(Continued)

FOREIGN PATENT DOCUMENTS

SU    1180916    *   9/1985

OTHER PUBLICATIONS

Lebo et al; ARBUS I-V final report; Apr. 1970; Hospital Management Study, 1972, (08794-480); Dialog copy 1 page.*

Primary Examiner—John W Hayes
Assistant Examiner—Daniel P Vetter
(74) Attorney, Agent, or Firm—Patents +TMS, P.C.

(57) ABSTRACT

A method and a system for providing bed availability information via a computer network are provided. Specifically, a healthcare facility such as a nursing home, a retirement home or any other type of healthcare or extended care facility may provide bed availability information and other types of information to a database on a computer network whereby users of the computer network may access the information within the database. The user may use a search mechanism to find a particular facility best suited for the user or another individual. Further, if the user does not know what type of facility he or she requires or does not know how to identify appropriate facilities, questions may be presented, and an analysis may be carried out to assist in determining the type of facility desired. Further, the user may then contact the facility to reserve beds or make appointments.

10 Claims, 3 Drawing Sheets

U.S. PATENT DOCUMENTS

| | | |
|---|---|---|
| 5,995,937 A | 11/1999 | DeBusk et al. |
| 6,026,363 A | 2/2000 | Shepard |
| 6,026,417 A | 2/2000 | Ross et al. |
| 6,032,119 A | 2/2000 | Brown et al. |
| 6,035,276 A | 3/2000 | Newman et al. |
| 6,289,088 B1 * | 9/2001 | Bruno et al. ............... 379/143 |
| 6,356,874 B1 * | 3/2002 | Ohrn ............................ 705/6 |

* cited by examiner

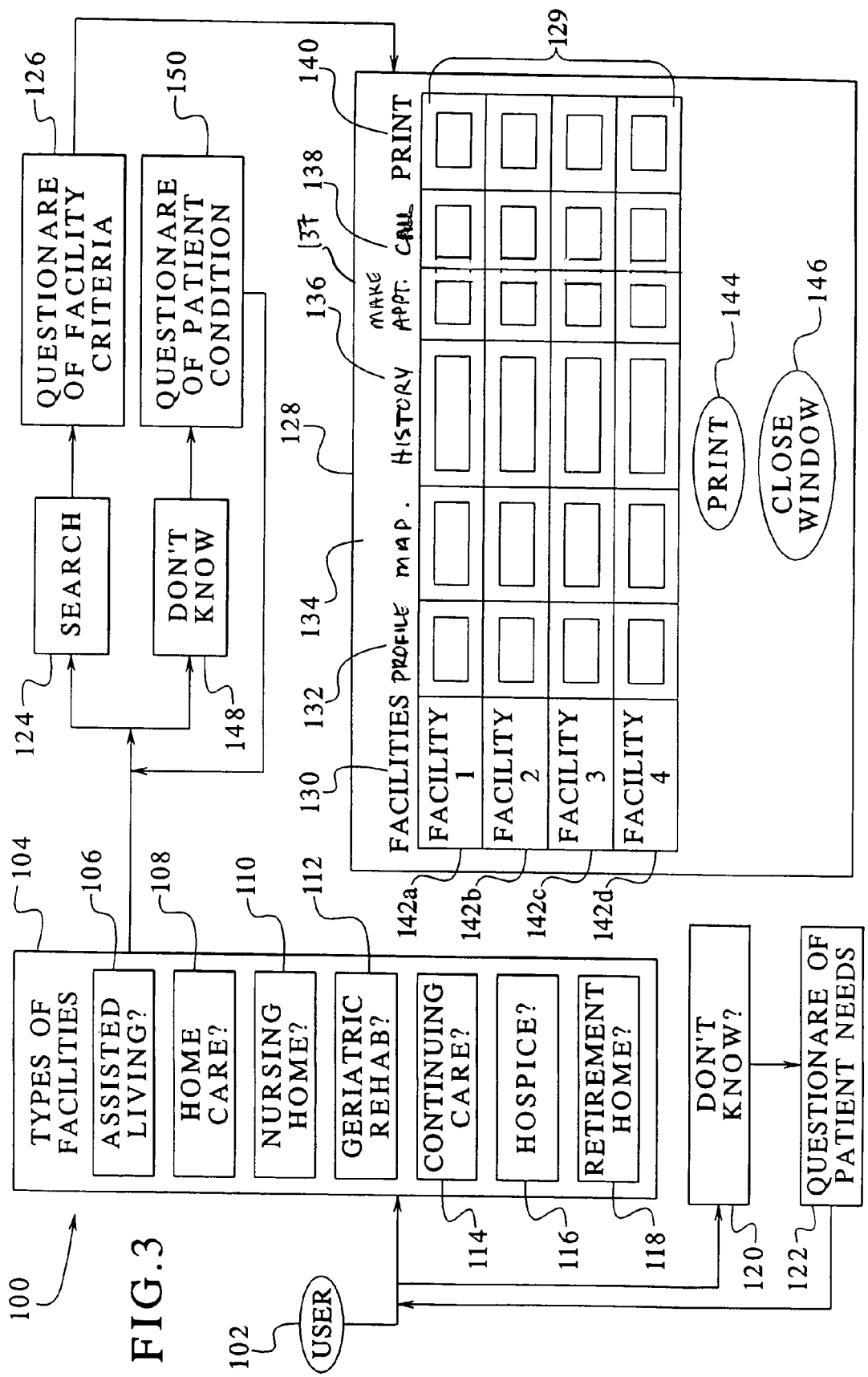

METHOD AND A SYSTEM FOR PROVIDING BED AVAILABILITY INFORMATION ON A COMPUTER NETWORK

BACKGROUND OF THE INVENTION

The present invention generally relates to a method and a system for providing bed availability information on, for example, a computer network. Further, the present invention relates to a method and a system for providing bed availability information on a computer network where a medical facility, such as, for example, a medical, health, extended care or geriatric care facility, may input information into a database regarding bed availability information of the particular facility. An individual requiring bed availability information may access the database and search the database for the bed availability information.

It is, of course, generally known to provide databases having information thereon. The information may be stored within the database for accessing the information at a later time. Further, it is generally known to provide access to databases on a computer network, such as, for example, the internet. A website may be utilized to simultaneously provide access to the database for adding information to the database and for retrieving information from the database.

Known methods of moving patients to beds in medical health facilities generally involve the placing of a telephone call to a medical health facility to determine if a bed or a plurality of beds is available for one or more patients. Further, known methods involve asking a plurality of questions to a representative of the medical health facility to determine types of beds available, types of services offered, payment method accepted and/or other information. These questions must be asked at each facility contacted to determine which facility best suits the patient. Moreover, many times, doctors and/or nurses must contact the medical health care facilities to gather the information about each facility. This may require doctors and/or nurses to spend more time performing an administrative task and less time providing care and support to patients and family members often regarding difficult and serious life and/or other health-related decisions.

Further, it is generally known to provide a website having access to a database wherein the database denotes whether beds are available at a healthcare facility. However, known websites and databases do not provide a mechanism for a user to directly contact the healthcare facilities to make appointments, to reserve a bed or beds and/or to gather further information about the facility.

Further, known databases and websites provide no information on the types of beds available, the quantity of beds available and/or a forecast of what beds may be available and when beds may be available in the future. Moreover, known databases and websites do not provide healthcare facilities access to the databases for adding or changing information regarding bed availability.

A need, therefore, exists for an improved method and a system for providing bed availability information in a database that overcome the problems associated with known methods and systems.

SUMMARY OF THE INVENTION

The present invention generally relates to a method and a system for providing bed availability information on a computer network. More specifically, the present invention relates to a method and a system for providing bed availability information on a computer network allowing a healthcare facility to input information regarding types of beds available, quantities of beds available and projections of bed availability in the future.

To this end, in an embodiment of the present invention, a method for providing bed availability information on a computer network is provided. The method comprises the steps of: providing a database; inputting bed availability information for a plurality of healthcare facilities having beds; and providing a first access to the database for finding the bed availability information by a user of the database.

In an embodiment, the database is provided on the network wherein access to the database is via the network.

In an embodiment, the network is the internet.

In an embodiment, one of the healthcare facilities is contacted after retrieving information about the healthcare facility.

In an embodiment, a remote server is provided and the database is stored on the remote server.

In an embodiment, a second access to the database is provided wherein an extended care or a healthcare facility having beds enters the bed availability information into the database via the second access.

In an embodiment, an individual healthcare facility accesses the database to input the bed availability information for the individual healthcare facility.

In an embodiment, the bed availability information includes a quantity of empty beds available.

In an embodiment, the bed availability information includes types of empty beds available.

In an embodiment, an internet-enabled form is provided on a website for accessing the remote database and inputting information into the database.

In an embodiment, the database is searched for the bed availability information and matches healthcare facility criteria with patient needs.

In an embodiment, individual information is entered related to a medical condition of a patient. The database is searched based on the individual information for the bed availability information.

In an embodiment, a search engine is provided for searching the database.

In another embodiment of the present invention, a system for storing and accessing bed availability information for a plurality of healthcare facilities is provided. The system has a computer network having a database associated with the network. Means is provided for inputting bed availability information of a plurality of healthcare facilities into the database. Further, means is provided for accessing the bed availability information and retrieving the bed availability information from the database.

In an embodiment, the bed availability information includes a quantity of beds available.

In an embodiment, the bed availability information includes types of beds available.

In an embodiment, the bed availability information includes a projection of expected availability of beds at a facility in a specified time frame.

In an embodiment, a remote server is provided wherein the database is contained on the remote server. A website provides access to the database.

In an embodiment, means is provided for accessing the database wherein an individual healthcare facility enters the bed availability into the database.

In an embodiment, means is provided for searching the database for the bed availability information of healthcare facilities.

It is, therefore, an advantage of the present invention to provide a method and a system for providing bed availability information on a computer network that provides access to the database via the internet.

A further advantage of the present invention is to provide a method and a system for providing bed availability information on a computer network that allows searching of the database via a search engine.

A still further advantage of the present invention is to provide a method and a system for providing bed availability information on a computer network that allows healthcare providers to input information into the database regarding their bed availability information.

Moreover, an advantage of the present invention is to provide a method and a system for providing bed availability information on a computer network that is accessed via a website.

Another advantage of the present invention is to provide a method and a system for providing bed availability information on a computer network that gives information concerning quantities and types of beds available as well as projections of bed availability in the future.

A still further advantage of the present invention is to provide a method and a system for providing bed availability information on a computer network that allows a user to securely transmit medical record information to facilities.

Additional features and advantages of the present invention are described in, and will be apparent from, the detailed description of the presently preferred embodiments and from the drawings.

BRIEF DESCRIPTION OF THE DRAWINGS

FIG. 3 illustrates a black box diagram of a decision tree and a results screen in an embodiment of the present invention.

DETAILED DESCRIPTION OF THE PRESENTLY PREFERRED EMBODIMENTS

The present invention relates to a method and a system for providing bed availability information on, for example, a computer network. Specifically, the present invention relates to method and a system for providing bed availability information on a computer network wherein a healthcare provider may provide bed availability information to a database and users of the database may choose a healthcare provider based on the information in the database.

Figure 1:
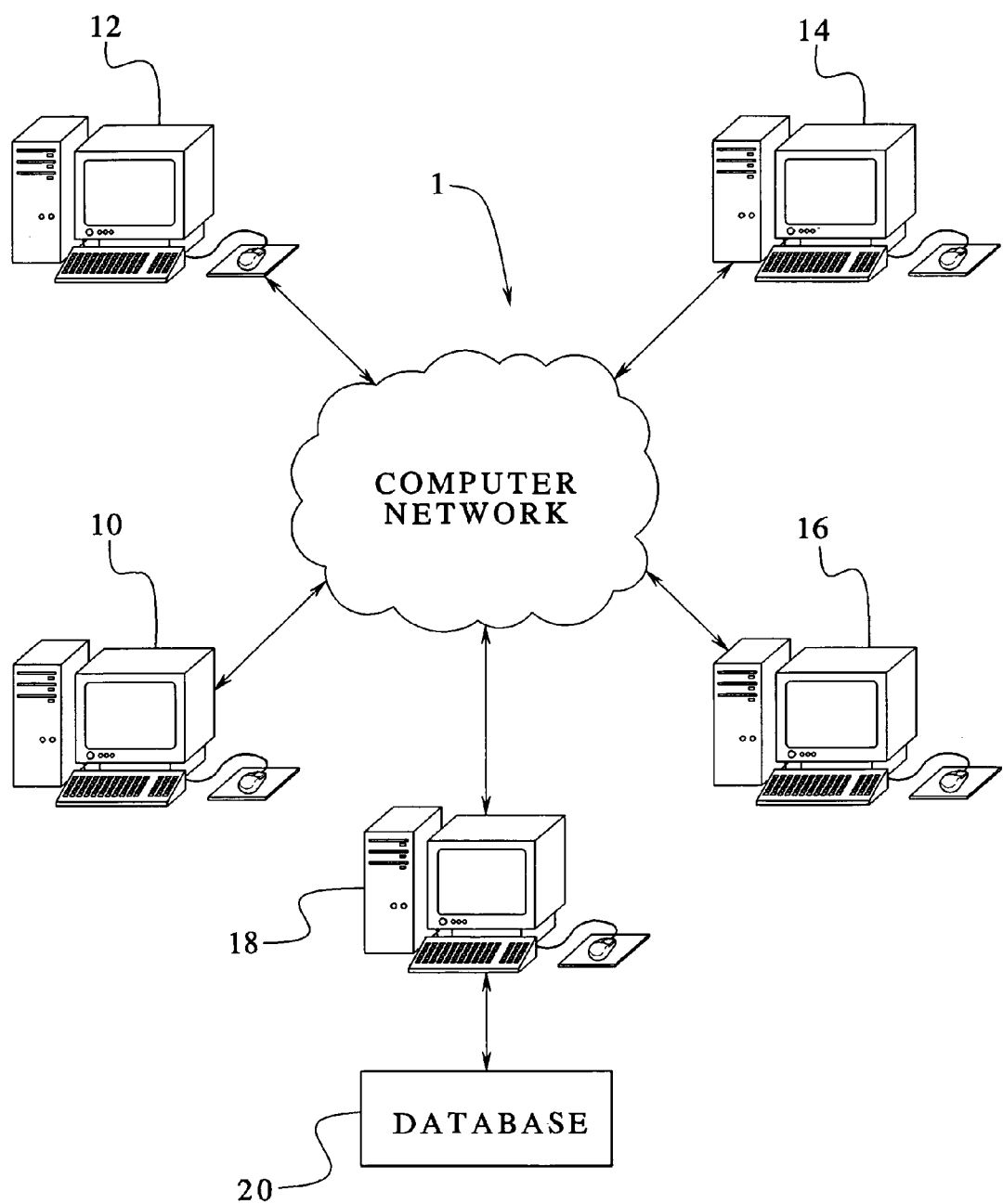
FIG. 1 illustrates a diagram of interconnected computers and a database in an embodiment of the present invention.

Referring now to the drawings wherein like numerals refer to like parts, FIG. 1 illustrates a computer network 1 having a plurality of computers 10-16 connected thereto. Further, the computer network 1 may include a server computer 18 having a database 20 attached thereto.

The computer network 1 may be any type of computer network that may interconnect a plurality of computers 10-16. Of course, any number of computers may be connected to the computer network and the invention should not be construed as limited as herein described. Further, the computer network 1 may be, for example, the internet wherein a plurality of remote computers are connected via a telephone network or other like network to each other. In addition, the computer network 10 may be an intranet wherein the plurality of computers 10-16 are connected via a network internal to an organization, such as a business, institution or the like. For example, the network may be connected via a LAN network. However, any computer network may be utilized that may be apparent to those skilled in the art.

The server computer 18 may include the database 20 associated therewith. The database 20 may contain information input into the database relating to bed availability information of healthcare providers. Any healthcare facility having bed availability information may use any of the computers 10-16 or any other computer connected via the computer network 1 to access the database 20 through the computer network 1. The healthcare facility may then enter the bed availability information into the database 20. A user of the database 20 desiring information concerning the availability of beds in a plurality of healthcare facilities could use any of the computers 10-16 or any other computer to access the database 20 and to extract the information concerning the availability of the beds of any of the healthcare facilities stored therein. The network 1, therefore, allows for real time updates and access to those updates regarding bed availability as a patient is checked in and subsequently checked out of the facility.

Further, any of the computers 10-16 may be a wireless system whereby the computer network may be accessed from a remote location. For example, any of the computers 10-16 may be a Palm Pilot™ by 3Com, Inc. that may access the internet wirelessly. Further, any of the computers 10-16 may be a wireless telephone having access to the internet.

Figure 2:
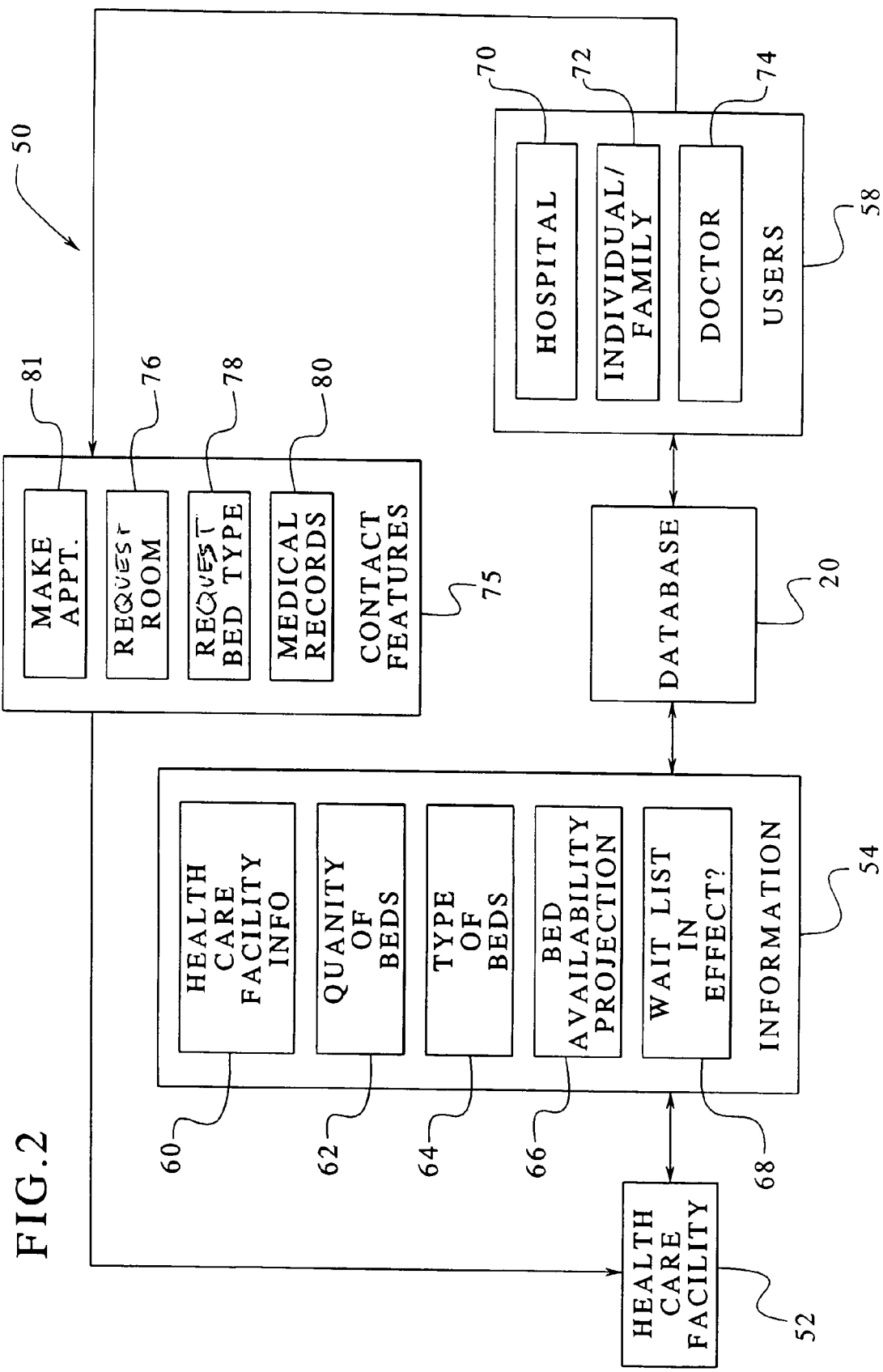
FIG. 2 illustrates a black box diagram of a healthcare provider and information that may be input into the database in an embodiment of the present invention.

FIG. 2 illustrates a black box diagram of a system 50. The system 50 includes a healthcare facility 52. Of course, any number of healthcare facilities may be included in the system 50. The healthcare facility 52 may be any type of healthcare facility, such as, for example, an assisted living facility, a home care facility, a nursing home facility, a geriatric rehabilitation facility, a continuing care facility, a hospice facility and/or a retirement home facility. Further, any other type of healthcare facility may be included in the present invention and is not meant to be limited as herein described.

The healthcare facility 52 may provide information 54 to the database 20 for a plurality of users 58 to download. The information 54 may include healthcare facility information 60, a quantity of beds 62 in the healthcare facility 52, types of beds 64 in the healthcare facility 52, a bed availability projection 66 in the healthcare facility 52 and whether a wait-list 68 is in effect in the healthcare facility 52. Further, any other information may be provided by the healthcare facility 52 to the database 20 as may be apparent to those skilled in the art.

The healthcare facility information 60 may include a map, contact information, details of the healthcare facility 52 and/or a history of the healthcare facility 52. In addition, any other type of information may be provided about the healthcare facility 52 that may be apparent to those skilled in the art to be stored in the database 20.

The types of beds 64 available in the healthcare facility 52 may include any type of bed that the healthcare facility offers, such as, for example, beds suited for. Alzheimer's disease patients, beds for intermediate care, beds with ventilators, beds in isolation, beds in negative air isolation, beds for males or females, single beds and/or luxury beds. Of course, other types of beds may be provided by the healthcare facilities that may be apparent to those skilled in the art.

The bed availability projection 66 may provide information concerning what the status of empty beds at a particular healthcare facility 52 may be in the future. For example, if the healthcare facility 52 has every bed full, the healthcare facility 52 may provide information that the a bed or a particular type of bed may be available within, for example, the following seven days. Of course, the bed availability projection 66 may provide information concerning the availability of beds at a healthcare facility for any specified time into the future such as, for example, days or weeks into the future.

The users 58 may have access to the database 20 and may retrieve the information 54 from the database 20. The users may include a hospital 70, an individual or a family 72 and/or physicians 74. However, the users 58 may include anyone who desires to retrieve the information 54 about the healthcare facility 52 from the database 20, and the present invention should not be construed as limited as herein described.

Upon receiving the information 54 about the healthcare facility 52 from the database 20, the user 58 may then contact the healthcare facility 52 via one of the contact features 75. The user 58 may, for example, request a room 76, request a bed type 78, transfer medical records 80 to the healthcare facility 52 and/or make an appointment 81 with the healthcare facility 52. Moreover, the user 58 may contact the healthcare facility 52 for any other reason that may be apparent to those skilled in the art.

The database 20 may be contained on a website or other graphical interface on the computer network that may provide electronic forms for the healthcare facility 52 to enter the information 54 into the database 20 or for the users 58 to obtain the information 54 from the database 20. Further, the healthcare facility 52 or the user 58 may have a website ID number and/or a password to maintain privacy and/or to change and save information input into the database 20 or taken from the database 20. The database 20 may be accessed via a single website or via a plurality of websites that are linked to the database 20.

FIG. 3 illustrates a navigation tree 100 whereby an individual user 102 may access a website or other graphical interface to begin the process of choosing a healthcare facility. The user 102 may choose from a plurality of types of facilities 104. The types of facilities 104 may include, for example, assisted living facilities 106, home care facilities 108, nursing home facilities 110, geriatric rehabilitation facilities 112, continuing care facilities 114, hospice facilities 116 and/or retirement home facilities 118. Further, any other healthcare facility may be included in the types of facilities 104 that may be apparent to those skilled in the art.

If, however, the user 102 does not know which type of healthcare facility 104 he or she may need, the user 102 may hit a "DON'T KNOW" button 120 within the graphical interface. The "DON'T KNOW" button 120 may then link the user 102 to a questionnaire of patient needs 122 whereby the user 102 answers a plurality of questions regarding the needs of the patient to be placed in the facility. The questionnaire of patient needs 122 may help the user 102 choose a type of facility that may be suited to the patient. Of course, the user 102 may be the patient seeking the type of facility. Alternatively, the user 102 may be an individual helping another in determining what type of facility may be best for the other.

The questionnaire of patient needs 122 may then be analyzed to determine and/or to recommend the type of facility needed by the user 102. The website may then link the user 102 to the particular type of facility that is recommended after answering the questions. Alternatively, the graphical interface may link the user 102 back to the types of facilities 104 thereby presenting the user 102 with the choice of the type of facilities the user 102 may desire.

The user 102 may choose a type of facility best suited for the user 102 or for another. After choosing one of the types of facilities 104, the user 102 may then search the database 20 via a search command 124 to find a particular facility or a plurality of facilities best suited for the user 102. The search command 124 may link the user 102 to a questionnaire of facility criteria 126 having a series of questions designed to find an individual facility or a plurality of facilities that match the particular criteria of the user 102.

For example, the questionnaire of facility criteria 126 may ask the user 102 to narrow the search to a particular geographic area. Further, the user 102 may input other information, such as, for example, concerning the payment method, type of facility, type of ownership, religious affiliation, population served, languages spoken, acceptance criteria, special units needed, service category needed, services needed and/or relationship with other entities. Further, other information may be used to narrow the choice of facility to one or any other number for the user 102 to choose.

After the user 102 inputs information into the questionnaire of facility criteria 126 and submits the information, a results window 128 may appear to show which facilities match the particular criteria of the user 102. The results screen 128 may include a table 129 showing facilities 130, profiles of the facilities 132, a map to the facility 134, a history of the facility 136, an option to make appointment 137, a call option 138 that allows the computer to immediately connect the user 102 to the facility via a telephone or telephone utility contained within the computer, or an option to print the information 140. The results screen 128 may include a facility 1 (142*a*), a facility 2 (142*b*) a facility 3 (142*c*), a facility 4 (142*d*) or any other facility that may be apparent to those skilled in the art that is matched by the search command 124.

The results screen 128 may include a print button 144 that may print the information of the facilities 130 as shown on the results screen 128. Further, the results screen 128 may include a "close window" button 146 that may close the results screen 128 of the graphical interface when the user 102 is finished viewing and/or printing the results screen 128. Still further, the user 102 may save the results of the search to easily access the results at a later time. In addition, the user 102 may compile lists of "favorite" healthcare facilities and save the lists in the database 20 to access at a later time.

Before the user 102 searches the database 20, the user 102 may desire a better understanding of how to match a patient's condition with the facility criteria. Therefore, a "DON'T KNOW" button 148 may be provided that may allow the user 102 to answer a plurality of questions in a questionnaire of patient condition 150. The questionnaire of patient condition 150 may include a plurality of questions related to the condition of the patient. An analysis of the answers to the questionnaire of patient condition 150 may be conducted to indicate to the user 102 what particular criteria the user 102 may be looking for in a particular facility. Further, the website may automatically search the database 20 for matching healthcare facilities based on the answers to the questionnaire of patient condition 150.

As indicated previously, the user 102 may be connected with the particular facility 130 to reserve a room 76, to reserve a bed type 78, to securely send medical records 80 thereto and/or to make an appointment 81 with the facility (as shown in FIG. 2).

Still further, if the user 102 decides to view the details 136 of the facility 130, the details 136 may indicate to the user 102 the quantity of beds provided, the types of bed provided, a bed availability projection or whether a wait-list is in effect for that facility 130. The user 102 may then use this information to find a bed in the particular facility 130 best suited for the user 102.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A method for providing bed availability information to a user wherein the user identifies an available bed for a patient and further wherein the bed availability information includes information on beds at a plurality of healthcare facilities wherein the plurality of healthcare facilities receives the patient based on the bed availability at one of the plurality of healthcare facilities, the method comprising the steps of:
    providing a computer network;
    providing a database connected to the computer network;
    inputting bed availability information for a plurality of healthcare facilities wherein each of the plurality of healthcare facilities have beds for providing a plurality of types of medical care and further wherein the bed availability information is input into the database and is accessible by the computer network;
    providing a first access to the database for determining the available bed for the patient by the user of the database;
    inputting a medical condition of the patient into the database;
    searching, by a computer in the computer network, the bed availability information for the plurality of healthcare facilities in the database;
    matching, by the computer in the computer network, the medical condition of the patient in the database to one of the types of medical care to obtain the bed availability information of the plurality of healthcare facilities based on each of the plurality of healthcare facilities having beds for providing one of the types of medical care to treat the medical condition of the patient; and
    determining, by the computer in the computer network, the available bed in the plurality of healthcare facilities for the patient with the medical condition from the bed availability information based upon the medical condition of the patient in the database.

2. The method of claim 1 further comprising the step of:
    providing the database on the network wherein access to the database is via the network.

3. The method of claim 1 wherein the network is the internet.

4. The method of claim 1 further comprising the step of:
    contacting one of the healthcare facilities after retrieving information about the healthcare facility.

5. The method of claim 1 further comprising the steps of:
    providing a remote server; and
    storing the database on the remote server.

6. The method of claim 1 further comprising the step of:
    providing a second access to the database wherein an extended care or a healthcare facility having beds enters the bed availability information into the database via the second access.

7. The method of claim 1 wherein an individual healthcare facility accesses the database to input the bed availability information for the individual healthcare facility.

8. The method of claim 1 wherein the bed availability information includes a quantity of empty beds available.

9. The method of claim 1 wherein the bed availability information includes types of empty beds available.

10. The method of claim 1 further comprising the step of:
    providing an internet-enabled form on a website for accessing the remote database and inputting information into the database.

* * * * *